United States Patent [19]
Schultz et al.

[11] Patent Number: 5,723,131
[45] Date of Patent: Mar. 3, 1998

[54] CONTACT LENS CONTAINING A LEACHABLE ABSORBED MATERIAL

[75] Inventors: Clyde L. Schultz, Ponte Vedra Beach; Ivan M. Nunez, Jacksonville; David L. Silor, Jacksonville; Michele L. Neil, Jacksonville, all of Fla.

[73] Assignee: Johnson & Johnson Vision Products, Inc., Jacksonville, Fla.

[21] Appl. No.: 580,233

[22] Filed: Dec. 28, 1995

[51] Int. Cl.$^6$ .............. A61K 9/00; A61F 13/00
[52] U.S. Cl. .............. 424/400; 424/422; 424/427; 424/429; 424/487
[58] Field of Search .............. 526/240, 304, 526/309, 548; 523/105, 106, 108; 424/400, 422, 427, 429, 487

[56] References Cited

U.S. PATENT DOCUMENTS

| | | | |
|---|---|---|---|
| 4,495,313 | 1/1985 | Larsen | 523/106 |
| 4,839,175 | 6/1989 | Guo et al. | 424/450 |
| 5,158,979 | 10/1992 | Clarkson, Jr. et al. | 514/575 |
| 5,236,969 | 8/1993 | Kunzler et al. | 523/108 |
| 5,256,751 | 10/1993 | Vanderlaan | 526/304 |
| 5,292,350 | 3/1994 | Molock et al. | 8/507 |
| 5,302,598 | 4/1994 | Clarkson, Jr. et al. | 514/275 |
| 5,311,223 | 5/1994 | Vanderlaan | 351/160 H |

*Primary Examiner*—Thurman K. Page
*Assistant Examiner*—Kathryne E. Shelborne

[57] ABSTRACT

A contact lens made of a polymeric hydrogel material having absorbed therein as a leachable additive of desferrioxamine, and a method for making the composition by soaking the polymeric material in a solution of the additive.

15 Claims, 13 Drawing Sheets

DFO SOLUTION ASSAY
(STAPHYLCOCCUS AUREUS)

5,723,131

CONTACT LENS CONTAINING A LEACHABLE ABSORBED MATERIAL

TECHNICAL FIELD

This invention relates to polymeric compositions employed to make contact lenses, the composition containing a polymeric hydrogel material and desferrioxamine as a leachable material absorbed in the polymeric material.

BACKGROUND OF THE INVENTION

It is known to employ hydrogel contact lenses to dispense therapeutic agents to the eye as disclosed in U.S. Pat. Nos. 3,787,378; 4,668,506; 4,713,244; 4,484,9:22; 4,931,279; and 5,213,801. It is not known, however, to employ desferrioxamine in contact lenses as the medicinal agent to kill or inhibit the growth of bacteria. Desferrioxamine has been employed as an anti-malarial agent for humans, but not as an agent delivered from a contact lens into the lachrymal fluids of the eye.

It is an object of this invention to provide a contact lens containing absorbed desferrioxamine that is leachable into the liquid surrounding the eye. It is another object to provide a contact lens that is capable of leaching sufficient desferrioxamine into the ocular liquid to substantially inhibit the growth of the bacteria present. Still other objects will become apparent from the more detailed description which follows.

BRIEF SUMMARY OF THE INVENTION

This invention relates to a polymeric composition comprising a polymeric hydrogel material containing desferrioxamine (also referred herein as DFO) as an additive absorbed in the polymeric composition and leachable therefrom. The polymeric composition is especially useful as the material of a contact lens. A particularly advantageous embodiment of the invention is a contact lens of polymeric hydrogel material having desferrioxamine absorbed therein in an amount up to 400 mg/lens. The lenses which function best in this area are those that are hydrogels containing 35–60% water. At an ocular pH of about 7.0.–7.4 about 40% of the absorbed desferrioxamine can be leached into the lachrymal fluid to inhibit the growth of bacteria in the fluid.

This invention further relates to a contact lens for the eyes which is a shaped polymeric composition containing an anionic acrylic polymeric material having absorbed therein desferrioxamine, wherein the absorbed desferrioxamine is leachable into ocular fluid of an eye at the existing conditions of the eye and a contact lens for the eyes which is a shaped polymeric composition containing an anionic acrylic polymeric material absorbed into which is desferrioxamine that is leachable into ocular fluid at ambient conditions.

This invention further relates to a process for preparing a contact lens for use which comprises washing the lens in a saline solution; placing the washed lens in an aqueous solution of desferrioxamine in a concentration of 250 mg desferrioxamine/mL of solution at a pH of 7.0–7.4 for 60–80 hours; and removing the lens from the solution ready for use in an eye.

DETAILED DESCRIPTION OF THE INVENTION

Desferrioxamine (DFO) has not been studied as a bacterial growth inhibitor, although it has been used as an antimalarial agent on humans, on rats to initiate immunosuppression (U.S. Pat. Nos. 5,158,979 and 5,302,598) and generally as an iron chelating agent (U.S. Pat. Nos. 4,839, 175 and 4,863,964). A study of DFO led to a series of experiments designed to test the possibility of its absorbance in a contact lens and subsequent release to the eye to prevent bacterial growth.

At the beginning of this study experiments were run to determine the utility of DFO in inhibiting the growth of bacteria found in the eye.

EXAMPLE 1

DFO was tested for its ability to control the growth of organisms in solution. The growth medium was an aqueous solution containing 0.9% saline and 0.1% peptone at a pH of 7.1.

Figure 1:
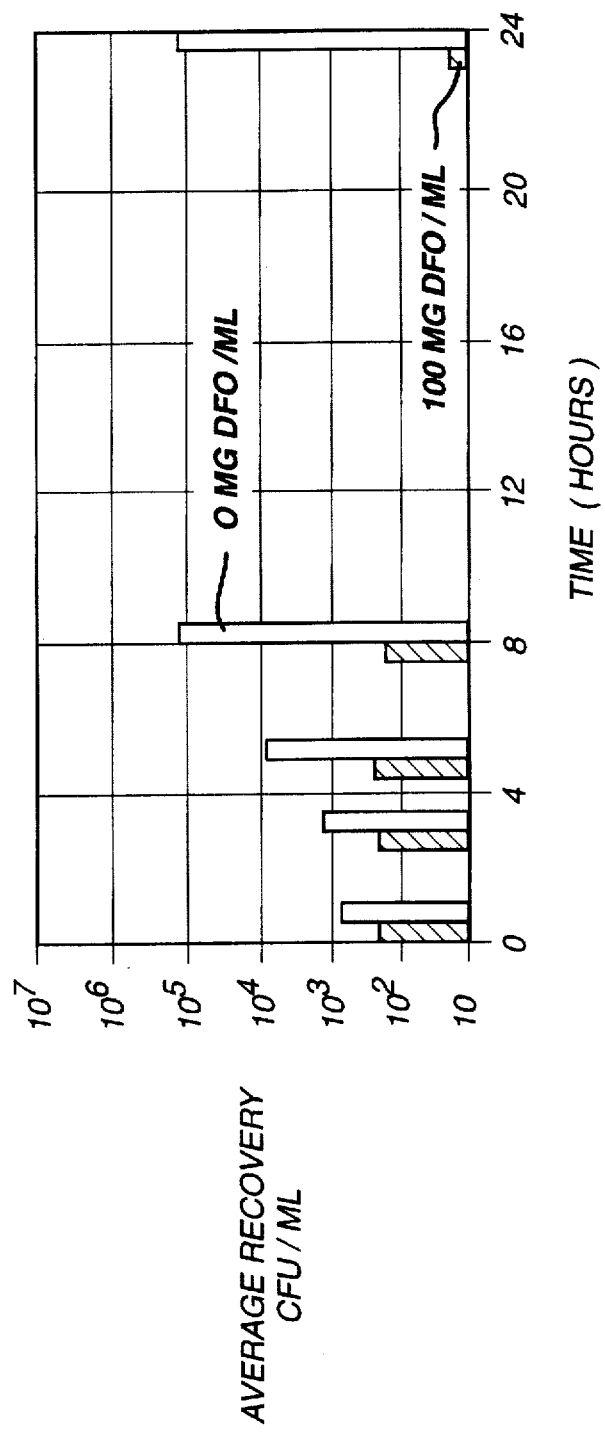
FIGS. 1 and 2 show the bacteriostatic effect of desferrioxamine.
Figure 2:
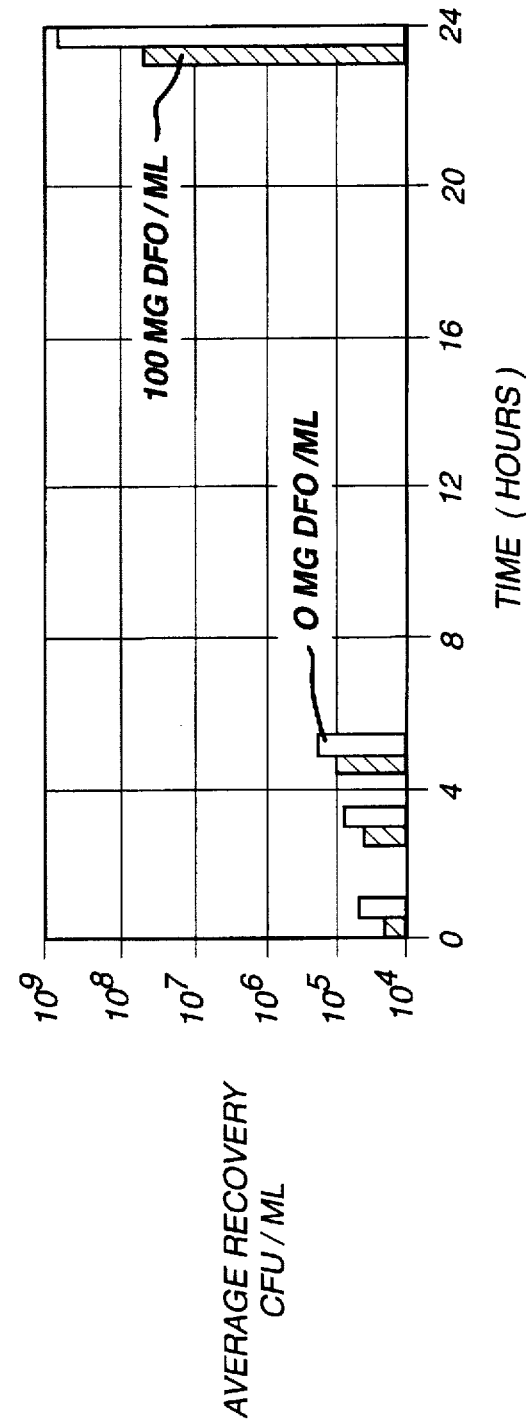

This growth medium was used as the control in the desferrioxamine solution assays. The experimental test solution consisted of the above growth medium plus 100 mg/mL of desferrioxamine with an adjusted pH of 7.1. Both control and experimental test solutions were filter sterilized through a 0.2 microns filter. The indicator organisms, *Staphylococcus aureus* (ATCC 6538) and *Pseudomonas aeruginosa* (ATCC (15442) were passaged overnight in the control growth medium at 35 degrees C. The following day, 0.5 mL of the respective indicator organism was added to 50 mL of the control and experimental test solution. Both solutions were then incubated at 35 degrees C with gentle agitation. Samples were collected at time points of 0, 3, 5, 8, and 24 hours. After making dilutions of the samples, TSA (Tryptic soy agar) pour plates were prepared and incubated at 35 degrees C overnight. Colony counts were performed the following day. The results demonstrating the bacteriostatic effect of desferrioxamine are shown in FIGS. 1 and 2. The results show a reduction of bacterial counts exposed to desferrioxamine as compared to bacteria not exposed to desferrioxamine beyond three hours of exposure. This was consistent for desferrioxamine in solution and released from a hydrogel lens. Statistically significant differences comparing desferrioxamine treated and untreated bacteria were observed for both species. CFU means colony forming units. The data showed that desferrioxamine released from a polymeric hydrogel lens materials are bacteriostatic to both Gram positive and Gram negative bacteria over time. This may reduce the numbers of bacteria sufficiently to abort a potential bacterial infection.

EXAMPLE 2

Contact lenses were prepared containing absorbed DFO, and those lenses were tested to see if the DFO might leach out of the lens and perform the bacterial growth inhibition as shown in Example 1. Polymeric hydrogel lenses containing approximately 60% water were soaked in a solution (0.9% saline) containing 100 mg/mL DFO for 72 hours and identified as experimental lenses. Control lenses were soaked for 72 hours in a solution (0.9% saline) containing no additive, and were identified as control lenses. The target organism used was *Staphylococcus aureus* (ATCC 6538). In this assay, one lens was added to 0.5 mL of the growth medium containing approximately 500 CFU/0.5 mL of the indicator organism. Three lenses (experimental and control) were set up for each time point. Samples were collected at time points of 0, 3, 5, 8 and 24 hours. After making dilutions of the samples, TSA pour plates were prepared and incubated at 35 degrees C overnight. Colony counts were determined the following day.

Figure 3:
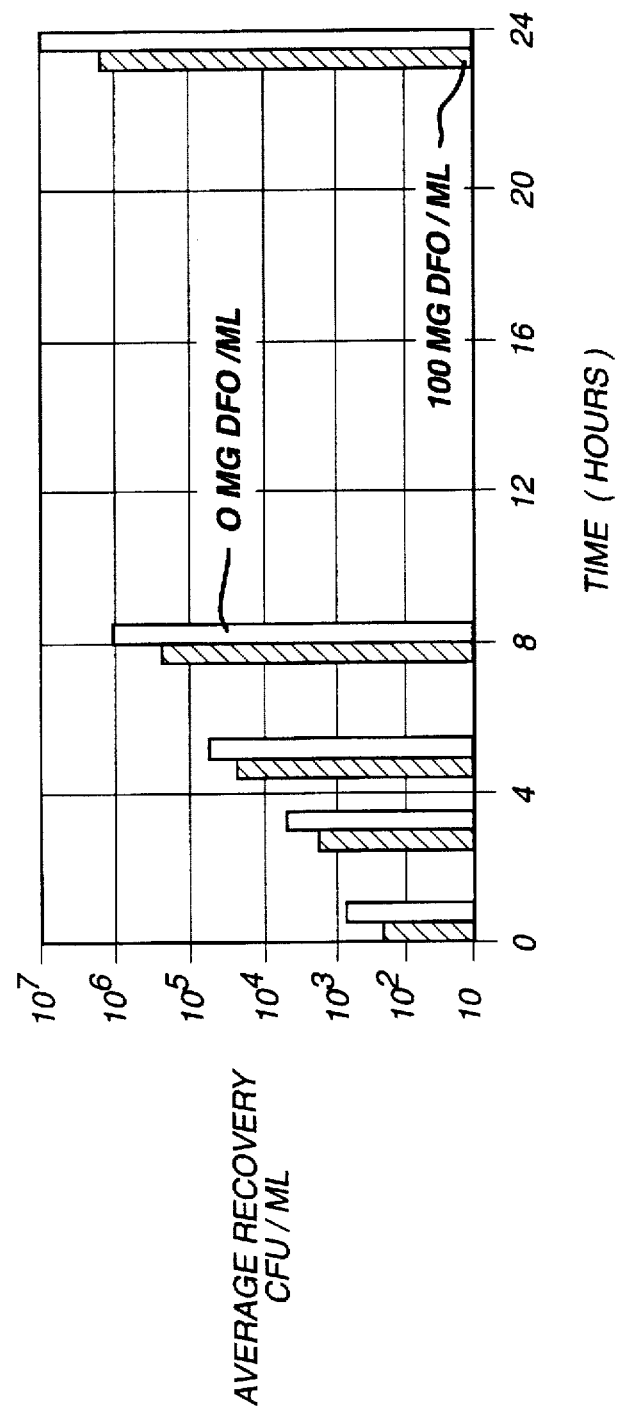
FIGS. 3 and 4 show the release of desferrioxamine from a contact lens.

FIG. 3 shows the release of DFO from a contact lens is active over a period of time and performs a significant growth control over bacteria.

Figure 4:
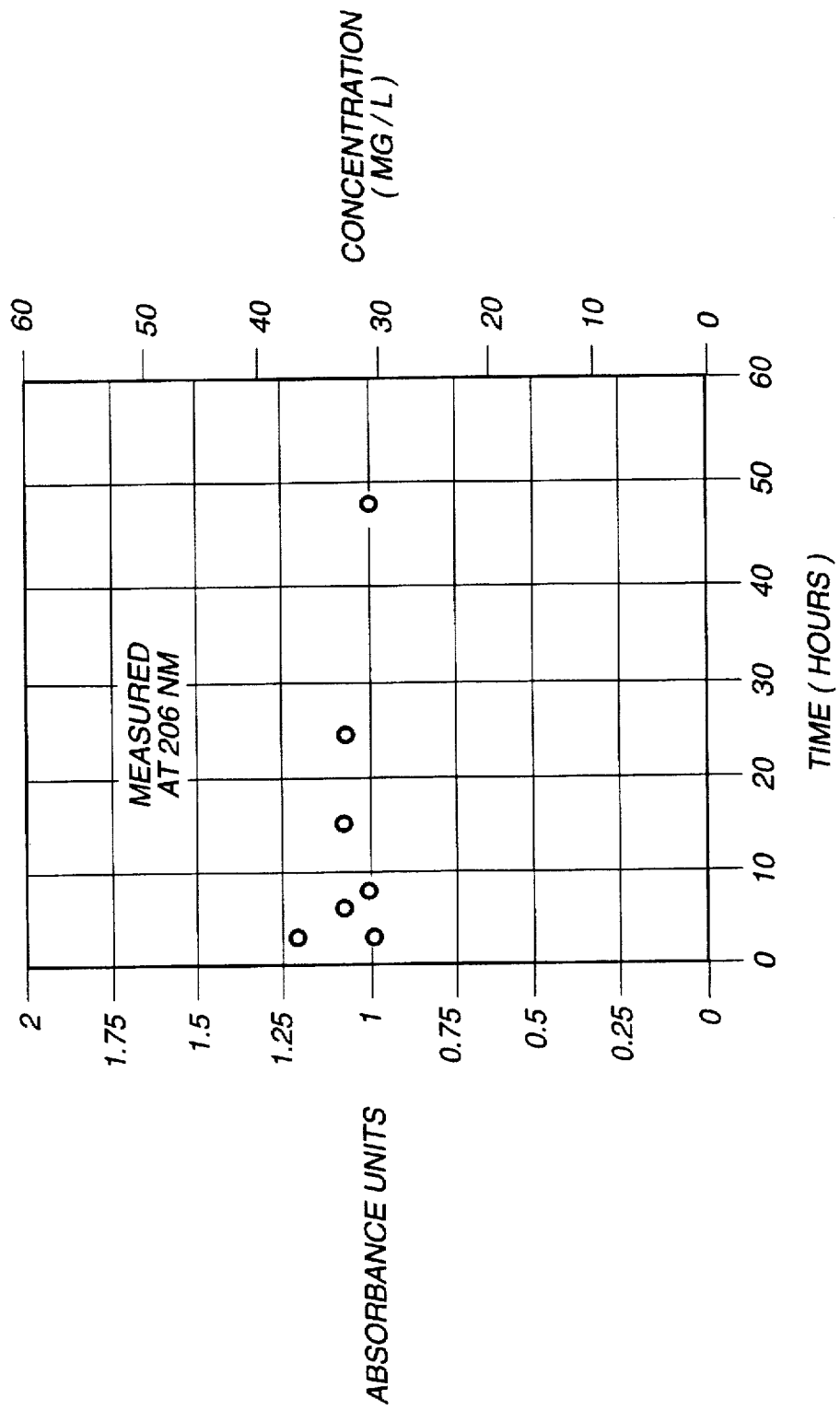

In FIG. 4 it can be seen that this system shows a consistent release of DFO over a long period of time; in that the system was still active after 50 hours of use. The released DFO is biologically active.

There have been no studies in the past of DFO being used in the eyes for control of bacterial growth. It has been known that if *Pseudomonas aeruginosa* is placed in the abraded eyes of rabbits an infectious bacterial keratitis will develop. It was decided to see if bacterial growth in the ocular environment could be controlled by the use of bactericides that might leach out of contact lenses. A series of experiments were run on cats and involving the following steps. Each cat would have one eye covered with an experimental lens and the other eye with a control lens, the former containing absorbed DFO and the latter containing no additive.

EXAMPLE 3

1. Experimental contact lenses were prepared by placing washed polymeric hydrogel lenses in 250 mg/mL desferrioxamine solution (pH 7.2) for 72 hours prior to use.

2. Immediately prior to use, all lenses were washed with saline.

3. Diluted *Pseudomonas aeruginosa* (15442) was added to the control eye of the cat (50 microliter).

4. The control lens was placed onto the control eye of the cat which had been gas anesthetized.

5. Another 50 microliter of bacteria was added to the control eye of a cat following the addition of the lens.

6. The control eye was taped closed.

7. Steps 2–6 were repeated on the experimental eye to which the experimental lens was placed.

8. The experiment was allowed to progress for four hours.

9. After this four hour period, the contact lenses were removed and the animals were allowed to wake-up and recover. The animals were examined for corneal edema, conjunctivitis and exudate production.

10. The lenses were removed, placed in saline solution and processed by sonication to recover bacteria.

11. The experiment was conducted with three different inoculum concentrations; $8 \times 10^4$, $1 \times 10^7$ and $1 \times 10^8$. There were four animals per group.

12. Animal eyes were examined histopathologically for evidence of pathology.

Figure 5:
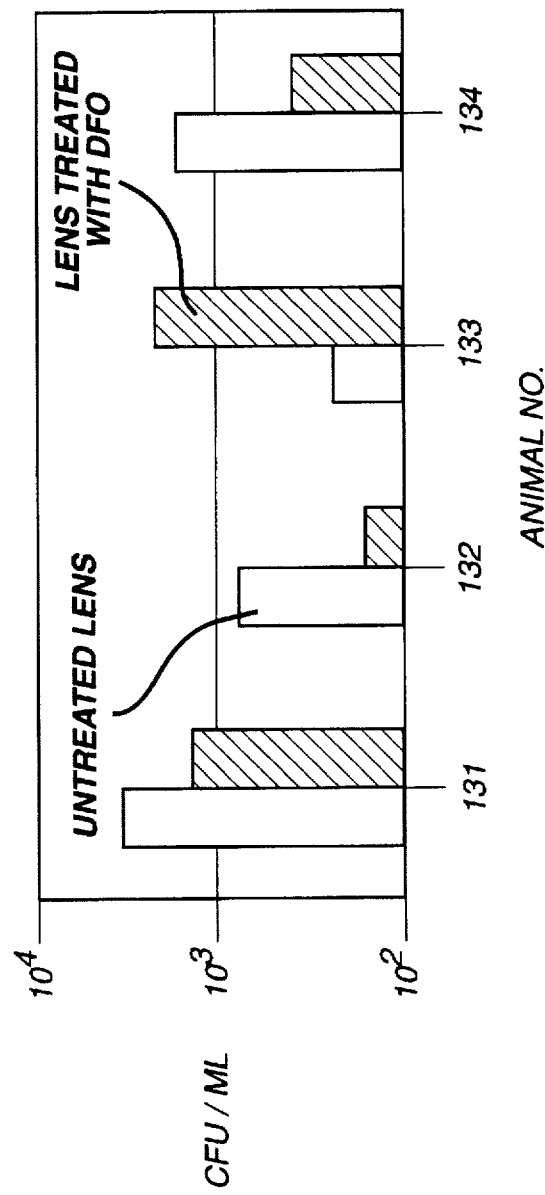
FIGS. 5, 6 and 7 show the desferrioxamine efficacy on animal eyes.
Figure 6:
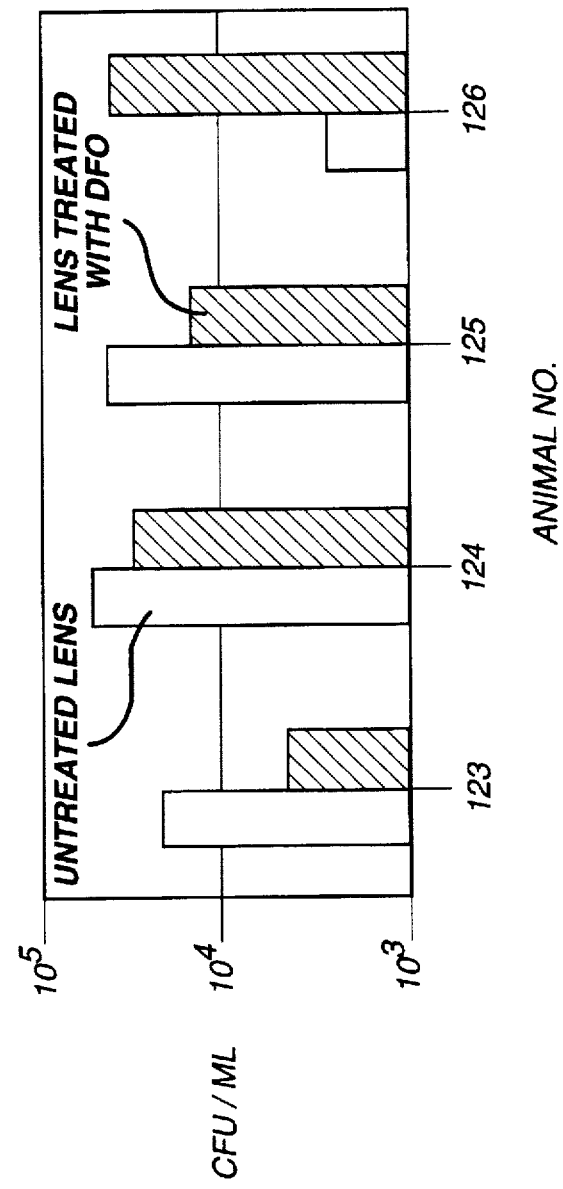
Figure 7:
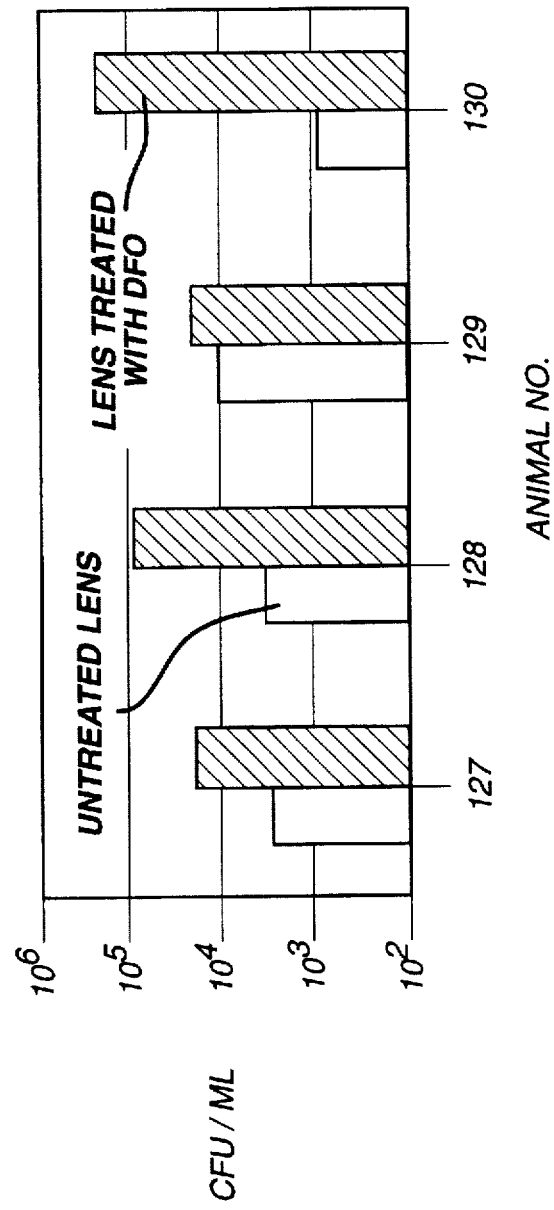

The results are shown in FIGS. 5–7.

The two lowest inoculum groups showed a decrease in bacterial counts of at least 60% in 6 of 8 animals when the bacterial counts of the control eye were compared to the experimental lens containing eye (FIGS. 5 and 6). One animal died due to a reaction to the gas anesthesia (133) and one animal showed an increased number of bacteria on the experimental lens (126). Necropsy revealed a systemic infection unrelated to the experimental model. The four animals in the highest inoculum group showed no change or increases in counts when the bacterial recovery was compared between control and experimental lenses (FIG. 7). This indicated that there were so many bacteria present that it was not possible to control their number. However, at the lower inoculum levels it was possible to control the bacterial population. The average number of bacteria recovered as a difference between control and experimental lenses in FIG. 5 was $2.6 \times 10^4$. The average number of bacteria recovered as a difference between control and experimental lenses in FIG. 6 was $1.4 \times 10^3$. Other authors have shown that active corneal infections may develop with an inoculum of $1.0 \times 10^4$ CFU of *Pseudomonas aeruginosa*. Animals may be symptomatic with as few as $1.0 \times 10^3$ CFU.

Histopathological examination of eye tissue did not reveal any overt pathological changes either in experimental or control animals.

The data indicated that DFO may be delivered from polymeric hydrogel materials in sufficient quantity to reduce bacterial populations during a closed eye period. However, it is possible to add bacterial inoculum in sufficient quantity to overwhelm the positive effects of DFO. This was seen in the highest inoculum group. The results of this experiment confirm the data obtained from in vitro experiments with DFO either delivered from a lens, or free in solution. It should also be noted that the number of bacteria used in this work was artificially high. In a real world situation the starting inoculum for an infection would probably be less than $1 \times 10^3$ CFU/lens.

Gross examination of the animals following lens removal did not detect any unusual morphological changes of the animal eyes. This appeared to be true regardless of the inoculum level. This indicates that neither the DFO or the high inoculum levels perturbed the ocular environment to any great degree up to four hours. Other authors have shown that gross infections will occur should the cornea or conjunctiva be compromised.

The available human clinical information suggests that worldwide most people who have adverse responses due to contact lens wear have non-infectious immunological reactions or acute immune syndrome or noninfectious peripheral ulcers. However, in certain countries the rates of infections due to bacterial contamination appear to be somewhat higher. In these countries a strategy for reducing live bacterial counts would be appropriate. This may be done by passive mechanisms, such as a non-biological adhesive lens, or actively by the addition of some anti-microbial agent.

It has been shown using an animal model that an anti-microbial agent may be delivered from a hydrogel contact lens material that is efficacious in reducing bacterial counts in vivo. The level of reduction is such that most infections may be aborted prior to the onset of frank disease. The data indicate that this agent appears to be safe to ocular tissue.

EXAMPLE 4

Figure 8:
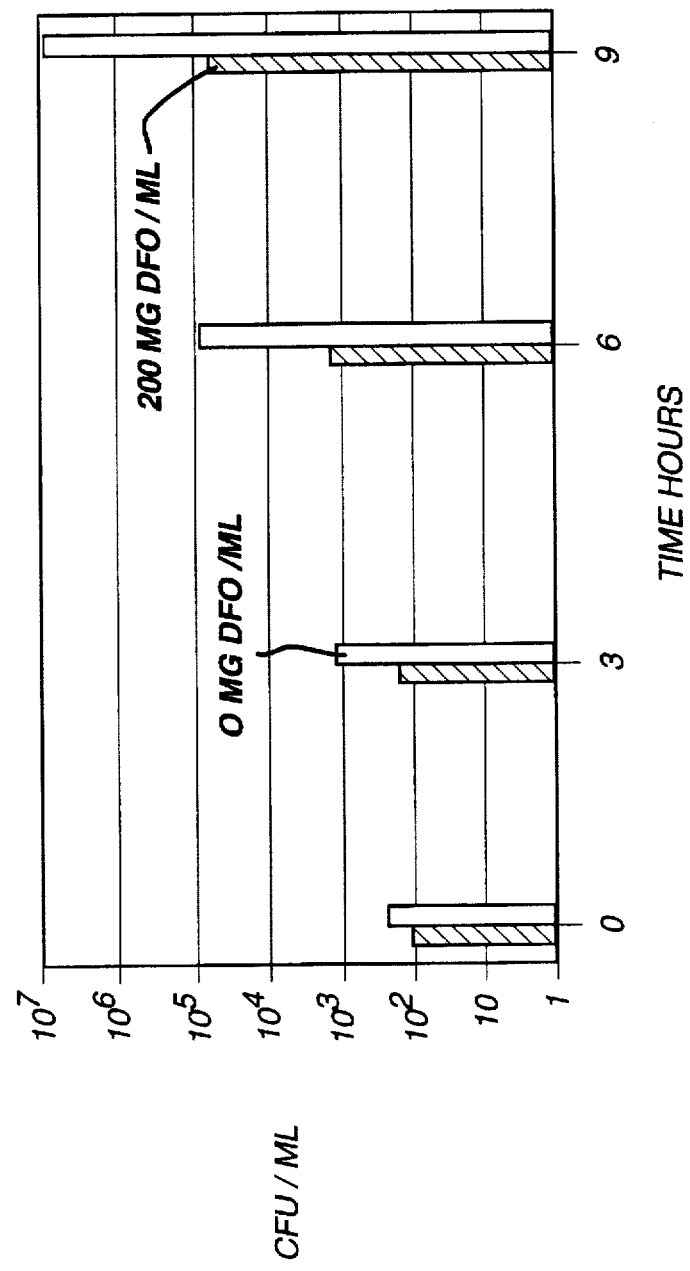
FIG. 8 shows the release of desferrioxamine from a contact lens.
Figure 9:
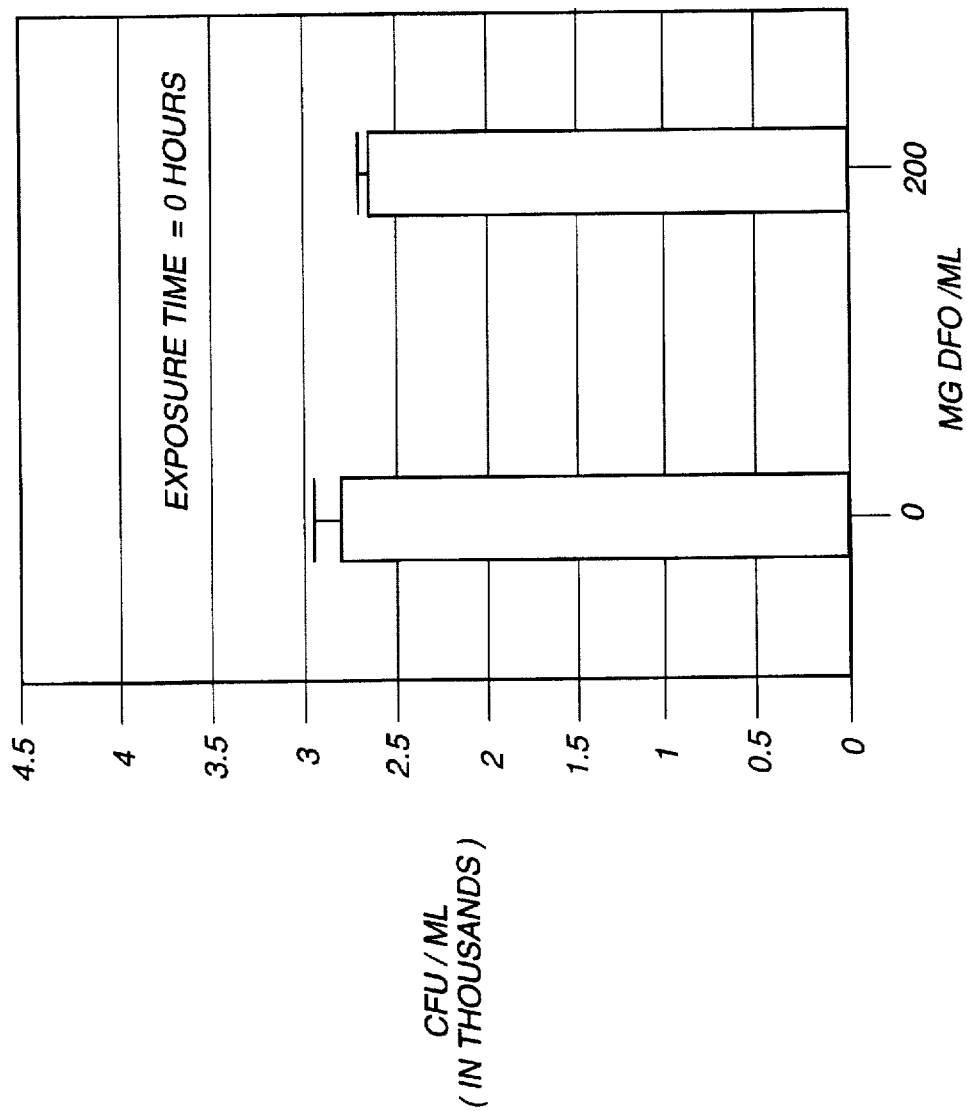
FIG. 9, 10, 11 and 12 show the effectiveness of desferrioxamine released from a contact lens to inhibit the growth of bacteria.
Figure 10:
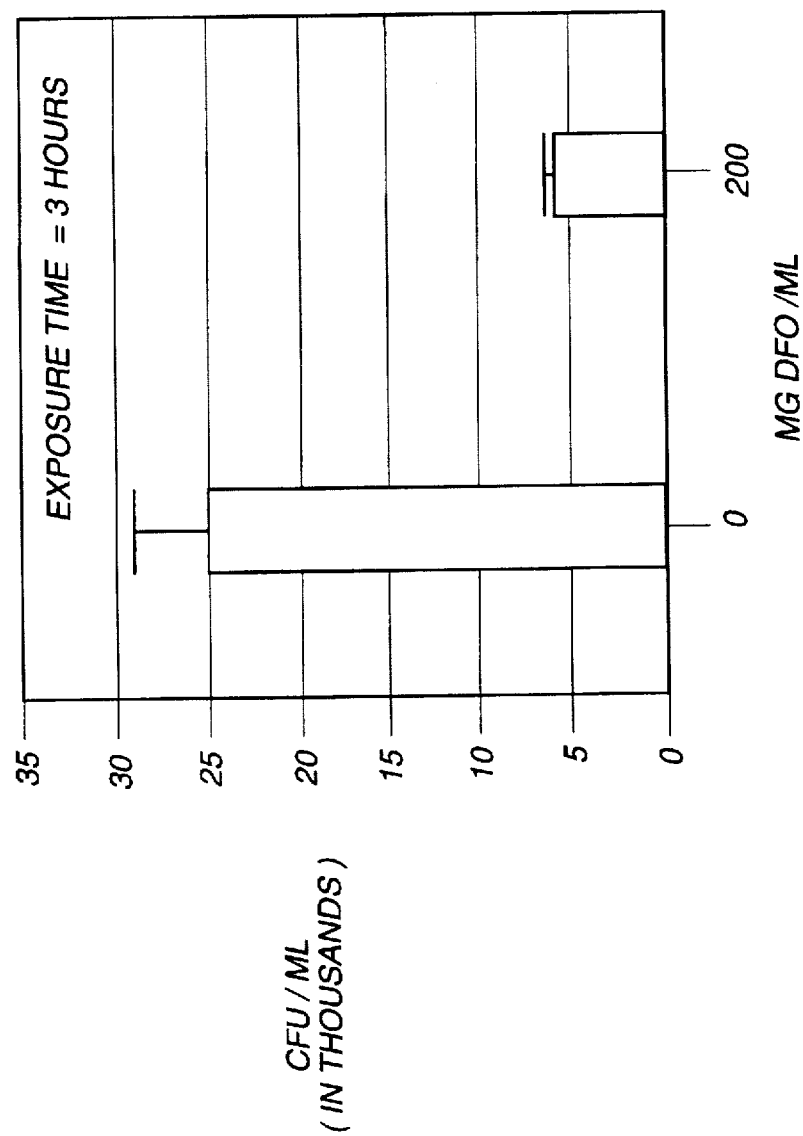
Figure 11:
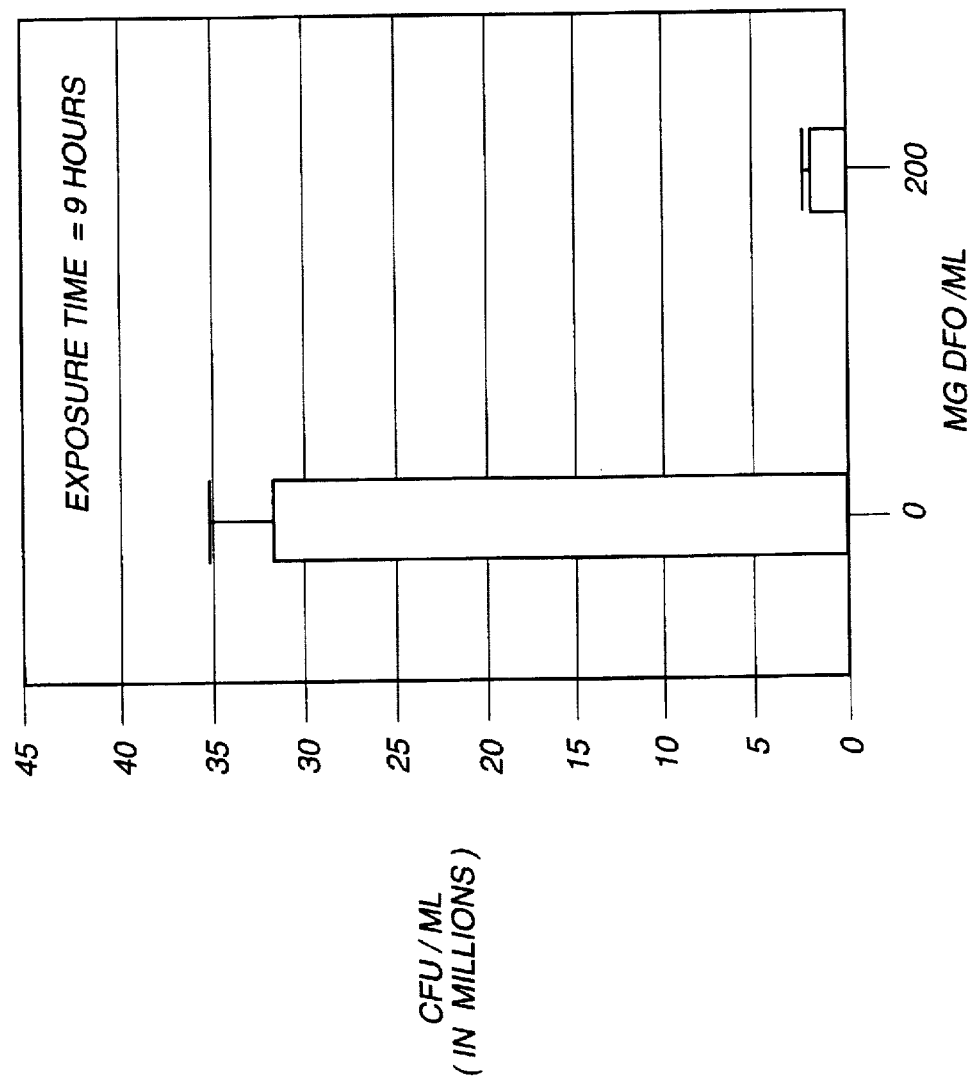
Figure 12:
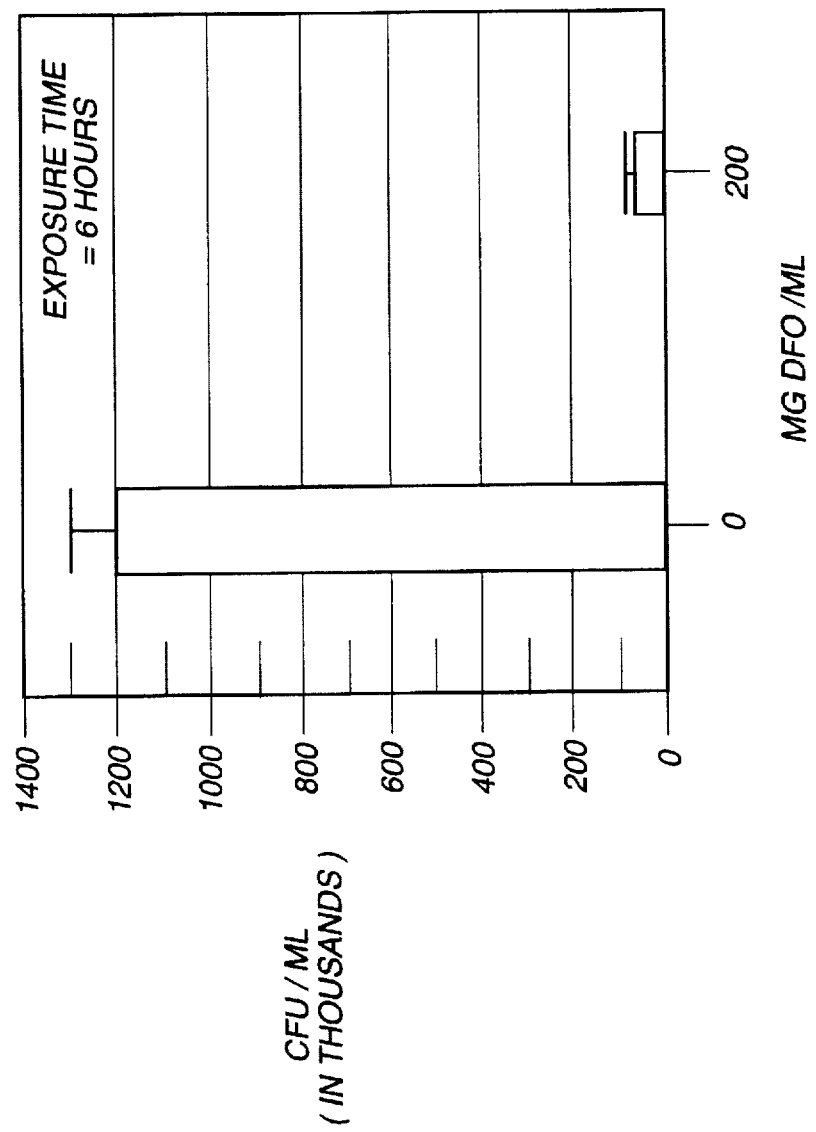

The same procedure as set forth in Example 3 was repeated and the lenses were tested against *Pseudomonas aeruginosa*. Similar results were obtained by comparing FIG. 8 with FIG. 4.

EXAMPLE 5

A series of experiments were run to study the effectiveness over different time periods of the system in releasing DFO to inhibit the growth of bacteria. In each instance the bacteria studied were *Pseudomonas aeruginosa* (15442). The control lens was treated with no DFO while the experimental lens was treated in a solution containing 200 mg DFO/mL. The results are shown in FIGS. 9–12 representing 0, 3, 6, and 9 hours respectively. The measurement shows the amount of colony forming units (CFU) remaining in the solution at the end of the treatment time. It will be seen that there is a large difference between the growth inhibition by the DFO-treated lens as compared to the control lens. The T-shaped object at the top of each bar shows the standard deviation from the observed value.

EXAMPLE 6

Figure 13:
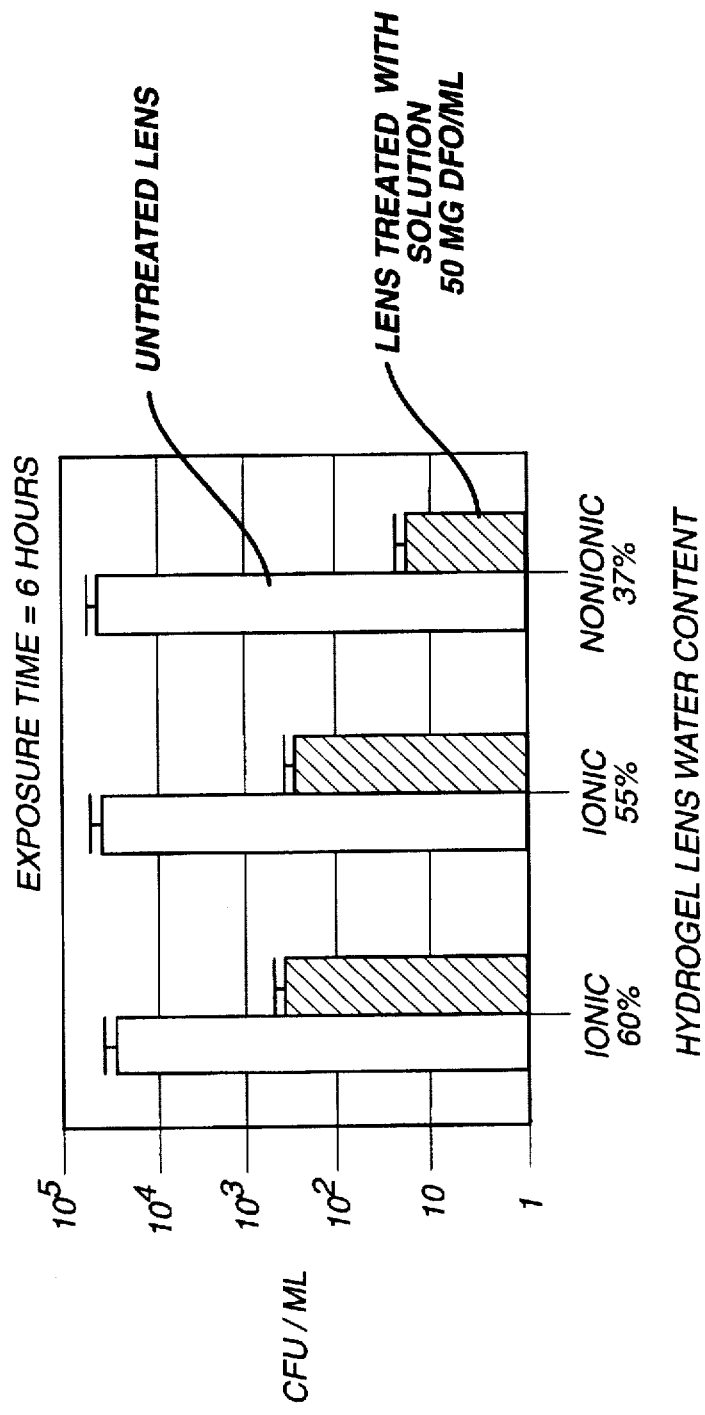
FIG. 13 shows the release of desferrioxamine for different contact lens compositions.

A similar series of tests were run to test the applicability of different types of contact lenses as the carrier for DFO. The procedure of Example 2 was repeated employing four different types of polymeric hydrogel lenses, differing particularly in water content or polymer type. In each instance a control with no DFO was compared to a lens containing leachable DFO prepared by soaking the lens in a solution of 50 mg DFO/mL for 72 hours. It will be seen in FIG. 13 that the lower water content polymeric materials (water content= 35–55%) are effective in releasing DFO. One sample of high water content (70%) showed no effect at all, and was not included in the chart.

This invention is directed principally at the absorption and leaching of DFO as a bacterial growth inhibitor. The basic concept of employing a contact lens to dispense a medical component is known, but if one considers the practicality of the invention, the lens must be a polymeric hydrogel of low water content (35–60%), and the medical component must be capable of being absorbed into the lens in sufficient quantity to form a reserve that will leach out at a generally consistent rate over a period of time, e.g., up to 24 hours. Other types of materials that might be absorbed into a contact lens and leached out into the lachrymal fluids include antibiotics, tissue healing agents, and anti-inflammatory agents. Some of these will function properly and other will not because of their chemical and physical properties. Desferrioxamine, however, is a preferred additive in this invention.

The polymeric material of this invention is a polymeric hydrogel which has been described in the prior art (e.g., see U.S. Pat. No. 5,256,751) as a hydrophilic polymer capable of forming a hydrogel when contacted with water. Examples of monomers forming hydrophilic polymers are hydroxyesters of acrylic or methacrylic acid, methycrylic acid (MAA), hydroxyethyl methacrylamide (HMA), DMA, NVP, styrene sulfonic acid, and other hydrophilic monomers known in the art.

Examples of hydroxyesters of acrylic or methacrylic acid include HEMA, hydroxyethyl acrylate (HEA), glyceryl methacrylate, hydroxypropyl methacrylate, hydroxypropyl acrylate and hydroxytrimethylene acrylate. The preferred hydroxyester is HEMA.

The most preferred hydrophilic monomer is HMA.

The relative proportion of the monomeric components depends on numerous factors, for example, the specific monomeric components chosen, and the final properties of the polymer desired, and can be readily determined empirically. Generally, the weight ratio of the hydrophilic monomer to the acyclic monomer is between about 1.5:1 to about 9:1, preferably about 2:1 to about 4:1, more preferably about 2.5:1 to about 3.5:1. If the amount of the hydrophilic monomer were greater than about 90%, then the resultant polymer will not show good mechanical properties (strength). On the other hand, if the amount of the hydrophilic monomer were less than about 60%, then the water content and oxygen permeability of the resultant hydrogel polymer will not be sufficiently high.

Additionally, as described in U.S. Pat. No. 5,292,350, polyfunctional crosslinking monomers, such as ethylene glycol dimethacrylate (EGDMA) and trimethylolpropane trimethacrylate (TMPTMA), can be used as comonomers in relatively small amounts in the reaction mixture to improve the dimensional stability and other physical properties of the lens. Similarly, other components may be added for specific applications, for example, to impart UV absorbing properties to the lens. Other similar disclosures of polymeric hydrogels are found in U.S. Pat. Nos. 4,495,313; 5,311,223 and other patents.

For the purposes of the present invention it is important that the water content of the hydrogel is about 35–60% by weight. The polymer may be ionic or nonionic; anionic polymers are not operable. Preferred polymer compositions are terpolymers of hydroxymethylmethacrylate, ethylene glycol dimethacrylate, and acrylic or methacrylic acid.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed is:

1. A polymeric composition comprising a polymeric hydrogel material containing desferrioxamine which is absorbed in said polymeric hydrogel material and capable of being leached into the ocular fluid.

2. The composition of claim 1 wherein at least 40% by weight of said desferrioxamine is capable of being leached out of said polymeric hydrogel material.

3. The composition of claim 1 wherein said ocular liquid has a pH at about 7.0–7.4.

4. The composition of claim 1 as a shaped contact lens.

5. The composition of claim 4 wherein said desferrioxamine is capable of being leached out to an extent of not more than about 400 mg per lens.

6. The composition of claim 1 wherein said polymeric hydrogel material is a terpolymer of hydroxyethylmethacrylate, ethylene glycol dimethacrylate, and acrylic acid.

7. The composition of claim 1 wherein said polymeric hydrogel material is a terpolymer of hydroxyethylmethacrylate, ethylene glycol, dimethacrylate, and methacrylic acid.

8. A contact lens for the eyes which is a shaped polymeric composition containing an anionic acrylic polymeric material having absorbed therein desferrioxamine, wherein the absorbed desferrioxamine is leachable into ocular fluid of an eye at the existing conditions of the eye.

9. A contact lens for the eyes which is a shaped polymeric composition containing an anionic acrylic polymeric material absorbed into which is desferrioxamine that is leachable into ocular fluid at ambient conditions.

10. The lens of claim 9 which contains desferrioxamine in any amount up to 400 mg/lens.

11. The lens of claim 9 wherein said polymeric composition is a polymeric hydrogel containing 35–60% water by weight.

12. The lens of claim 9 wherein said acrylic polymeric material is a terpolymer of hydroxyethylmethacrylate, ethylene glycol, dimethacrylate, and acrylic acid.

13. The lens of claim 9 wherein said ocular fluid has a pH of 7.0–7.4.

14. A process for preparing a contact lens for use which comprises washing the lens in a saline solution; placing the washed lens in an aqueous solution of desferrioxamine in a concentration of 250 mg desferrioxamine/mL of solution at a pH of 7.0–7.4 for 60–80 hours; and removing the lens from the solution ready for use in an eye.

15. The composition of claim 1 wherein said polymeric hydrogel material has a water content of about 35–65% by weight.

* * * * *